United States Patent [19]  
Dickinson

[11] 4,065,471  
[45] Dec. 27, 1977

[54] N-(4-AMINO-2-BUTYNYL)IMIDES

[75] Inventor: William B. Dickinson, Colonie, N.Y.

[73] Assignee: Sterling Drug Inc., New York, N.Y.

[21] Appl. No.: 72,169

[22] Filed: Sept. 14, 1970

Related U.S. Application Data

[60] Continuation-in-part of Ser. No. 5,368, Jan. 23, 1970, abandoned, and a continuation-in-part of Ser. No. 881,302, Dec. 1, 1969, abandoned, which is a continuation-in-part of Ser. No. 650,587, July 3, 1967, abandoned, and a continuation-in-part of Ser. No. 650,633, July 3, 1967, abandoned, each is a division of Ser. No. 447,105, April 9, 1965, Pat. No. 3,354,178.

[51] Int. Cl.² ............... C07D 207/12; C07D 207/06; C07D 211/88

[52] U.S. Cl. ............ 260/326 N; 260/239 D; 260/239 DD; 260/239.3 R; 260/251 GN; 260/326.25; 260/326.37; 260/326.5 FM; 260/326.81; 260/293.69; 424/246; 424/248.53; 424/267; 424/274; 544/41; 544/42; 544/46; 544/62; 544/73; 544/102; 544/104; 544/141; 544/144

[58] Field of Search ............... 260/326.5 FM, 326 N, 260/326.3, 239.3 R, 293.69, 247.2 R, 243 B, 281 GN, 326.25

[56] References Cited

U.S. PATENT DOCUMENTS 3,354,178 11/1967 Dickinson ............... 260/326.5 X  
3,444,171 5/1969 Dahlbom et al. ............... 260/281

Primary Examiner—Paul M. Coughlan, Jr.  
Assistant Examiner—Mary C. Vaughn  
Attorney, Agent, or Firm—William G. Webb; B. Woodrow Wyatt

[57] ABSTRACT

N-(4-Amino-2-butynyl)imides are prepared from N-propargylimides, paraformaldehyde and the appropriate secondary amine. The compounds are useful as stimulants or depressants of the central nervous system.

8 Claims, No Drawings

N-(4-AMINO-2-BUTYNYL)IMIDES

This application is a continuation-in-part of my copending applications Ser. Nos. 5,368 (filed Jan. 23, 1970) and 881,302 (filed Dec. 1, 1969), both abandoned, which in turn are continuations-in-part of my copending applications Ser. Nos. 650,587 and 650,633, both filed July 3, 1967, both abandoned, both said applications S.N. 650,587 and 650,633 being divisions of my prior application S.N. 447,105, filed Apr. 9, 1965, now U.S. Pat. 3,354,178, patented Nov. 21, 1967.

This invention relates to novel compositions of matter known in the art of chemistry as aminoalkynes and derivatives thereof and to methods for their preparation.

In one of its aspects, the invention sought to be patented resides in the concept of a class of chemical compounds which I designate as N-(4-amino-2-butynyl)-N-alkylcarboxamides. I depict these compounds as having a molecular structure corresponding to general Formula I,

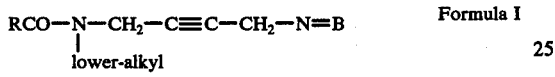

Formula I wherein R is selected from the group consisting of H and loweralkyl and N=B is a basic tertiary amine moiety.

As used herein the term N=B means a basic tertiary amine moiety; that is, the amino nitrogen atom bears two substitutents which do not materially affect the basicity of the amine moiety as a whole, or the two substituents are joined to form a ring, with the same result. Such amines are well known to those skilled in the art. For example, it is known that lower-alkyl groups, lower-alkenyl groups, and cyclo-alkyl groups do not detract from the basicity of an amine when they replace hydrogen on the amine nitrogen. Moreover, it is known that cyclic amines wherein two of the valence bonds of the amine nitrogen atom are joined by an alkylene bridge, forming a heterocyclic ring, are relatively strong bases, and as such are suitable for the purposes of my invention.

Hence by the group —N=B, L mean amines which are preferably selected from the group consisting of di(lower-alkyl)-amino, N-lower-alkyl-N-lower-alkenylamino, di(lower-alkenyl)amino, N-lower-alkyl-N-cycloalkylamino, di(cycloalkyl)amino, N-(phenyl-lower-alkyl)-N-lower-alkylamino, pyrrolidino, piperidino, morpholino, thiamorpholino, 2,5-dimethylpyrrolidino, and the like.

As used herein, the term "lower-alkyl" means saturated, monovalent aliphatic radicals, including straight and branched-chain radicals, of from one to six carbon atoms. For purpose of illustration only and not being limited thereto, lower-alkyl is represented by methyl, ethyl, propyl, isopropyl, butyl, tert.-butyl, sec.-butyl, amyl, hexyl and the like.

As used herein "lower-alkenyl" means monovalent aliphatic radicals of from three to seven carbon atoms, which contain at least one double bond, and are either straight or branched-chain. Among lower-alkenyl radicals are included, for purpose of illustration, allyl, methallyl, crotyl, 1-(2-hexenyl), and the like.

As used herein "cycloalkyl", means cyclic saturated aliphatic radicals of from three to eight carbon atoms. For purpose of illustration the term cycloalkyl includes, but is not limited to, cyclopropyl, cyclobutyl, 2-methylcyclobutyl, cyclopentyl, cyclohexyl, 4-methylcyclohexyl, cyclo-octyl, and the like.

As used herein "phenyl-lower-alkyl" means a monovalent radical consisting of a phenyl nucleus bonded to the rest of the molecule through a divalent lower-alkylene radical of from one to six carbon atoms. The phenyl nucleus thereof may bear low molecular weight substituents without adversely affecting the ultimate properties of the compound as a whole, as further described below. For purpose of illustration, such substituents are represented by lower-alkyl, lower-alkoxy, lower-alkylmercapto, halo, trifluoromethyl, amino, and the like.

In another of its aspects, the invention sought to be patented resides in the concept of a class of chemical compounds which I designate as N-(4-amino-2-butynyl)lactams. I depict these compounds as having a molecular structure corresponding to general Formula II.

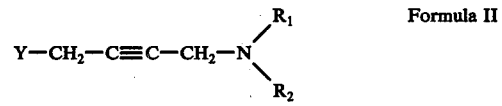

Formula II wherein Y is a lactam radical bonded to the remainder of the molecule through the lactam nitrogen atom. Thus the radical Y is represented by the general formula,

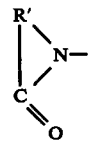

wherein R' is a divalent bridge having from three to five atoms in the chain. The divalent bridge as an alkylene radical which can be interrupted by a hetero atom of the class consisting of —O—, —S—, —NH— and —N(lower-alkyl)—. For purpose of illustration, the lactam group Y is exemplified by, but not limited to, the following: 2-oxopyrrolidino, 2-oxopiperidino, 2-oxohexamethyleneimino, 3-oxomorpholino, 3-oxothiamorpholino, 2-oxo-oxazolidino, 2-oxo-piperazino, 4-methyl-2-oxopiperazino, and the like.

In Formula II, $R_1$ and $R_2$ can be the same or different and are selected from the class consisting of H, lower-alkyl, lower-alkenyl and phenyl-lower-alkyl, each as defined above.

In still another of its aspects, the invention sought to be patented resides in the concept of a class of chemical compounds which I designate as N-(amino-aliphatic)-pyrrolidinones. I depict these compounds as having a molecular structure represented by the Formula III,

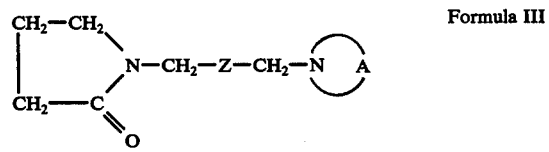

Formula III wherein A is a divalent bridging radical having from 5 to 7 atoms in the chain and Z is a divalent bridging radical having its valence bonds on adjacent carbon atoms. The divalent bridging radical, A, is an alkylene radical which can be interrupted by a member of the class consisting of —O—, —S—, —NH—, and —N(-lower-alkyl)-radicals. The group

according to this definition, thus includes for purpose of illustration, but is not limited to, the following: piperidino, 4-methylpiperidino, hexamethyleneimino, heptamethyleneimino, morpholino, 2-methylmorpholino, thiamorpholino, piperazino, 4-methylpiperazino and the like.

The divalent bridge, Z, is an aliphatic chain having its valence bonds on adjacent carbon atoms and is saturated or unsaturated. The term Z thus represents, alkylene, for example,

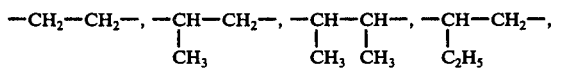

and the like; vinylene, for example,

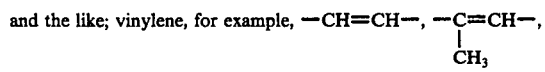

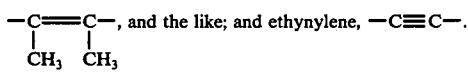

In yet another of its aspects, the invention sought to be patented resides in the concept of a class of chemical compounds which I designate as N-(4-amino-2-butynyl)imides. I depict these compounds as having a molecular structure corresponding to the Formula IV,

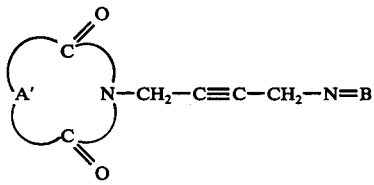

wherein A' is a member of the group consisting of a divalent alkylene radical of from two to four carbon atoms and an ortho phenylene radical and N=B is as defined above. In Formula IV, the group

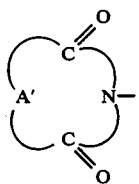

is a cyclic imide radical of from five to seven ring members. The cyclic imide radicals are illustrated by, but not limited to, succinimido, glutarimido, adipimido, pyrotartarimido, 2,3-dimethylsuccinimido, phthalimido, 5-methoxyphthalimido, 5-methylphthalimido, 4,5,6,7-tetrachlorophthalimido, 4-butoxyphthalimido, 5-methylmercaptophthalimido, 4-bromophthalimido, and the like.

In still another aspect, the invention sought to be patented resides in the concept of a class of chemical compounds which I designate as N-(4-amino-2-butynyl)heterocyclic amines. I depict these compounds as having a molecular structure corresponding to Formula V,

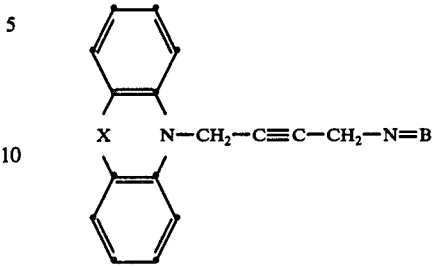

Formula V wherein N=B is an amine group as defined above for Formula I, and X is a member of the group consisting of S, O, —CH=CH—, —N=N—, and —CH$_2$—CH$_2$—. In this aspect, the compounds of the invention are 1,4-diamino-2-butynes, wherein one of the amino moieties is a tricyclic heterocycle selected from the group consisting of 10-phenoxazinyl, 10-phenothiazinyl, 5-dibenz[b,f]-azepinyl, 11H-dibenzo[1,2,5]triazepinyl, and 5-(10,11-dihydro)-dibenz[b,f]azepinyl.

Formulas IV and V encompass compounds which have one or two benzene rings incorporated therein. Here and elsewhere throughout this specification, it will be understood that the benzene ring can be unsubstituted, or it can bear one or more substituents of low molecular weight and of such nature that they do not interfere or take part in the preparative reaction. When substituted, the benzene ring has from one to four substituents which can be in any of the available positions of the ring, and where more than one substituent is present, they can be the same or different, and they can be in any of the various position combinations relative to each other. The substituents preferably have a molecular weight of less than 150. Examples of such substituents, for the purpose of illustration but without limiting them thereto, include lower-alkyl, lower-alkoxy, lower-alkylmercapto, lower-alkylsulfinyl, lower-alkylsulfonyl, halogen, nitro, trifluoromethyl and cyano, wherein lower-alkyl is as previously defined.

The manner and process of making and using my invention will now be generally described so as to enable a person skilled in the art of chemistry to make and use the same, as follows:

The final products of the foregoing aspects of this invention, as exemplified by general Formulas I, II, III and IV, can be prepared by the following general procedures. A carboxylic acid amide or imide having at least one hydrogen atom attached to the nitrogen atom thereof is caused to react in an inert solvent at a temperature less than 30° C., preferably about room temperature, with a propargyl halide, for example propargyl bromide, in the presence of a strong base to form the N-propargyl amide (or imide). The nature of the inert solvent is not critical, but I prefer to use toluene, benzene, or ether. The intermediate N-propargyl amide (or imide) is then caused to react with formaldehyde and an amine, which contains at least one hydrogen atom attached to the nitrogen atom thereof, under conditions well-known to the art for carrying out the Mannich reaction with acetylenes. I prefer to employ a trace of cuprous chloride as a catalyst in the Mannich reaction.

The compounds of the invention represented by Formula V (i.e., bearing a tricyclic amine structure) are prepared in the same manner as the above compounds. That is, the tricyclic amine, bearing a secondary amine nitrogen, is caused to react with propargyl bromide in the presence of a strong base (acid acceptor) and the N-propargyltricyclic amine is then caused to react with formaldehyde and a secondary amine in the conventional Mannich reaction procedure.

In the above procedure, the nature of the strong base is not critical, but it must be at least as strong a base as sodium hydroxide. Examples of suitable strong bases include sodium hydride, sodium amide, lithium amide, sodium ethoxide, potassium tert.-butoxide, tetramethylammonium methoxide, sodium hydroxide, and the like.

The final products of my invention are usually obtained in their free base form as yellowish or colorless oils which may be distilled at reduced pressure without decomposition. While the compounds are basic substances and can form acid-addition salts or quaternary ammonium salts with strong acids or organic esters thereof, respectively, I have found that the salt forms are difficult to obtain in crystalline form. I therefore prefer to isolate the products of my invention in their free base form.

The final products of my invention, as exemplified by general Formulas I, II, III, IV and V are useful as pharmacodynamic agents. In particular, compounds in this group have been found useful for their stimulating effect on the central nervous system, as evidenced by reversal and prevention of reserpine-induced ptosis in mice. Compounds in this group are also effective central nervous system depressants, as evidenced by hexobarbital potentiation and antagonism toward pentylenetetrazole activity in mice. In the central nervous system depressant tests, compounds in this series showed a superior spectrum of activities and gave more reliable results than did reference compounds in the art.

That is, all of the compounds of Formulas I, II, III, IV and V have been found to possess both C.N.S. stimulant and C.N.S. depressant activities as determined by the above-indicated reversal and prevention of reserpine-induced ptosis test, which is a standard pharmacological test for determining C.N.S. stimulant activity, and by the above-indicated hexobarbital potentiation and anti-pentylenetetrazole tests, which are standard tests for determining C.N.S. depressant activity.

While it may appear at first blush that C.N.S. depressant and stimulant components of action are mutually exclusive actions and cannot be present simultaneously in the same compound, in fact it is well known that the occurrence of such components in the same species is commonplace in C.N.S. active compounds, and Goodman and Gilman in *The Pharmacological Basis of Therapeutics*, Third Edition, The Macmillan Company, New York, N.Y., page 39 (1965) classify such drugs as "Drugs Which Selectively Modify C.N.S. Function", which they describe as being drugs which "may give evidence of both (depressant and stimulant) effects simultaneously" . It is moreover known, as taught for example by Chen in *Evaluation of Drug Activities: Pharmacometrics* (Edited by Laurence and Bacharach), Vol. 1, pages 239-244 (1964), that a number of well known C.N.S. active agents, such as iproniazid, imipramine, and amytryptyline, possess such dual depressant-stimulant components. Chen further teaches that such activities are determined in laboratory animals using the same pharmacological test procedures used in evaluating the instant compounds, namely the reserpine-induced ptosis prevention and the anti-pentylenetetrazole tests.

Examination of the compounds produced by the processes described above, and more particularly described in the Examples below, by nuclear magnetic resonance and infrared spectrographic analysis reveals spectral data confirming the molecular structure set forth herein. These physical characteristics, taken together with the nature of the starting materials, the mode of synthesis, and the correspondence of calculated and found values of elemental analyses of representative samples positively confirm the structure of the compositions sought to be patented.

The best mode contemplated by the inventor of carrying out his invention will now be set forth as follows:

EXAMPLE 1A

N-Methyl-N-propargylacetamide

To a mixture containing 23 g. (0.5 mole) of sodium hydride (52% suspension in mineral oil) in 600 ml. of toluene was added a solution containing 36.5 g. (0.5 mole) of N-methylacetamide over a period of 45 min. in a nitrogen atmosphere. The mixture was refluxed for 2.5 hr and allowed to cool to room temperature. A solution containing 60.0 g. of propargyl bromide in 100 ml. of toluene was added dropwise over a period of 1.5 hr. The mixture was allowed to stir at room temperature overnight. It was then filtered, and the filtrate solvent was removed under reduced pressure. The residue was passed through a chromatographic column packed with silica gel. The product was eluted with a 1:1 ether-hexane mixture. Upon removal of the solvent the residual oil was distilled and redistilled. The product, N-methyl-N-proparglyacetamide, boiled at 53° at 0.8 mm.; $n_D^{25}$ = 1.4814.

EXAMPLE 1B

N-Methyl-N-(4-pyrrolidino-2-butynyl)acetamide

Under a nitrogen atmosphere, a solution containing 13.0 g. (0.12 mole) of N-methyl-N-propargylacetamide, 5.8 g. of paraformaldehyde, 10.5 g. (0.15 mole) of pyrrolidine and a trace of cuprous chloride in 80 ml. of dioxane was refluxed for 5 hrs. and allowed to stand overnight. The mixture was filtered remaining oil was distilled and redistilled giving N-methyl-N-(4-pyrrolidino-2-butynyl)acetamide, boiling at 120° C. at 0.03 mm.

EXAMPLE 2A

N-Propargylsuccinimide

To a solution containing 54 g. (1 mole) of sodium methoxide in 400 ml. of methanol as added a solution containing 99 g. (1 mole) of succinimide in 400 ml. of methanol under an atmosphere of nitrogen. During the addition, the reaction mixture was kept at about 25° C. by means of a water bath. The mixture was then refluxed for 30 min. and cooled to 20° C. with a water bath, giving a clear solution of sodium succinimide. To this solution was added dropwise a solution containing 132 g. (1.1 moles) of propargyl bromide in 100 ml. of methanol over a period of 1.5 hrs. The mixture was allowed to stir overnight and the solvent was removed under reduced pressure. Chloroform was then added to the residual oil, and the sodium bromide which precipitated was removed by filtration. The filtrate was passed through a chromatographic column packed with silica gel, and the product was eluted with methanol and ether. After removal of the solvent, the residual oil was distilled giving N-propargylsuccinimide, which boiled at 98° C. at 0.03 mm., $N_D^{25.5} = 1.5402$.

EXAMPLE 2B

N-[4-(1-pyrrolidinyl)-2-butynyl]-succinimide

Following the example given in Example 1B, 19.1 g. (0.15 mole) of N-propargylsuccinimide was caused to react with 6.3 g. of paraformaldehyde and 14.2 g. (0.2 mole) of pyrrolidine in 100 ml. of dioxane in the presence of a trace of cuprous chloride. The reaction was refluxed for 5 hrs. and allowed to stand overnight. After filtration of the reaction mixture and removal of the solvent from the filtrate, the residual oil was distilled to give N-[4-(1-pyrrolidinyl)-2-butynyl]-succinimide boiling at 155° C. at 0.04 mm. This product solidified, and after recrystallization from ether, melted at 93.0 to 94.0° C. (corr.).

EXAMPLE 3A

2-Chloro-10-propargylphenothiazine

To a solution containing 0.2 mole of butyllithium in 350 ml. of absolute ether (prepared in situ under nitrogen) were added 46.5 g. (0.2 mole) of 2-chlorophenothiazine while the mixture was maintained at $-10°$ C. The reaction mixture was then allowed to stir for forty-five minutes at 0° C. To the resulting solution of 2-chloro-10-phenothiazinyllithium were added 30 g. (0.25 mole) of propargyl bromide in 30 ml. of absolute ether. This reaction mixture was allowed to stir at room temperature overnight. After quenching with dilute hydrochloric acid, the ethereal phase of the reaction mixture was washed with water and dried over anhydrous calcium sulfate. Upon removal of the solvent a semi-solid mass of crude 2-chloro-10-propargylphenothiazine remained. Recrystallized from methanol and from ether-hexane, pure 2-chloro-10-propargylphenothiazine melted at 112.0°–115.0° C. The structure was confirmed by nuclear magnetic resonance spectroscopy.

EXAMPLE 3B

2-Chloro-10-[4-(1-pyrrolidinyl)-2-butynyl]phenothiazine

Following the procedure given in Example 1B, 2-chloro-10-propargylphenothiazine (21.7 g.; 0.08 mole) was caused to react with 3.8 g of paraformaldehyde and 7.1 g. (0.1 mole) of pyrrolidine in the presence of a trace of cuprous chloride in dioxane. Recrystallized from ether-hexane, the pure 2-chloro-10-[4-(1-pyrrolidinyl)-2-butynyl]-phenothiazine thus obtained melted at 48.0°–50.0° C.

The following compounds are obtained by the method given above:

10,11-Dihydro-5-[4-(1-pyrrolidinyl)-2-butynyl]-5H-dibenz[b,f]azepine, melting at 53.4°–54.2° C.;

5-[4-(Butylmethylamino)-2-butynyl]-10,11-dihydro-5H-dibenz[b,f]azepine, a yellow oil, $n_D^{25} = 1.5870$;

10,11-Dihydro-5-[4-(dimethylamino)-2-butynyl]-5H-dibenz[b,f]azepine, melting at 55.6°–56.8° C.;

5-(4-Piperidino-2-butynyl)-5H-dibenz[b,f]azepine;

11-(4-Pyrrolidino-2-butynyl)-11H-dibenzo[1,2,5]triazepine;

10-(4-Morpholino-2-butynyl)phenoxazine; and

10-[4-(Diisopropylamino)-2-butynyl]-2-trifluoromethylphenothiazine.

EXAMPLE 4

N-[4-(1-pyrrolidinyl)-2-butenyl]-pyrrolidinone.

A solution containing 24.7 g. (0.12 mole) of 1-(4-pyrrolidino-2-butynyl)-2-pyrrolidinone dissolved in 250 ml. of pyridine was hydrogenated in a bottle-type hydrogenator over 5 g. of 2% palladium-on-strontium carbonate catalyst. When the theoretical quantity of hydrogen was absorbed, the catalyst was removed by filtration and the solvent was removed under reduced pressure. Upon distillation and chromatographic separation, the product, N-[4-(1-pyrrolidinyl)-2-butenyl]-pyrrolidinone, was obtained as a clear oil distilling at 107° C. at 0.05 mm.

EXAMPLE 5

N-[4-(1-pyrrolidinyl)-butyl]-2-pyrrolidinone

A solution containing 21.0 g. (0.10 mole) of 1-(4-pyrrolidino-2-butynyl)-2-pyrrolidinone dissolved in 205 ml. of absolute ethanol was hydrogenated in a bottle-type hydrogenator over 0.6 g. of platinum oxide catalyst. When the theoretical quantity of hydrogen was absorbed, the catalyst was removed by filtration and the filtrate was removed under reduced pressure. Upon distllation, the product, N-[4-(1-pyrrolidinyl)-butyl]-2-pyrrolidinone, was obtained as a clear oil boiling at 118° C. at 0.05 mm.; $N_D^{25} = 1.4922$.

EXAMPLE 6

1-[4-(Diethylamino)-2-butynyl]pyrrolidine

Following the procedure given in Example 1B, 7.8 g. (0.07 mole) of diethylpropargylamine, 3.8 g. of paraformaldehyde, 5.7 g. (0.08 mole) of pyrrolidine, and a trace of cuprous chloride in 80 ml. of dioxane was refluxed for 4 hours and allowed to stand overnight. After distillation and redistillation, the product, 1-[4-(diethylamino)-2-butynyl]pyrrolidine was obtained as a clear oil boiling at 68.0° C. at 0.05 mm.; $N_D^{25} = 1.4770$.

The following intermediate products, N-propargyl-carboxamides, are also prepared according to the procedure given in Example 1A:

N-propargyl-2-piperidone, boiling at 81° C. at 0.5 mm;

N-propargylnicotinamide, m.p. 107.8°–109.8° C.;

N-propargyl-2-oxazolidinone, b.p. 102° C. at 0.06 mm;

4-propargyl-3-thiomorpholinone, b.p. 115° C. at 0.05 mm;

N-methyl-N-propargylpropionamide, b.p. 62.0° C. at 0.1 mm;

N-(3-methoxypropyl)-N-propargylformamide, b.p. 78.0° C. at 0.04 mm;

5-methyl-1-propargyl-2-pyrrolidinone, b.p. 75.0° C. at 1.0 mm;

N-propargylpropionamide, m.p. 66.0°–67.0° C.;

3,4,5-trimethoxy-N-propargylbenzamide, m.p. 165.0°–167.0° C.;

10,11-dihydro-5-propargyl-5H-dibenz[b,f]azepine, m.p. 105.0°–106.0° C.; and

2-Chloro-10-propargylphenothiazine, m.p. 112.0°–115° C.

The modification of the carboxylic acyl radical, the lower alkyl group and the amine moiety illustrated in general Formulas I-IV are further exemplified by the following embodiments of my invention:

N-Methyl-N-[4-(methylpropylamino)-2-butynyl]acetamide, which distilled at 101° C. at 0.05 mm;

N-Methyl-N-[4-(1-pyrrolidinyl)-2-butynyl]formamide, which distilled at 112° C. at 0.06 mm.;
N-Methyl-N-[4-(butylmethylamino)-2-butynyl]acetamide, which distilled at 105.0° C. at 0.08 mm.;
N-Methyl-N-[4-(dimethylamino)-2-butynyl]acetamide, which distilled at 83.0° C. at 0.1 mm.;
N-Methyl-N-[4-(butylmethylamino)-2-butynyl]formamide which distilled at 103.0° C. at 0.06 mm.;
N-Methyl-N-4-[4-(butylmethylamino)-2-butynyl]propionamide, which distilled at 112.0° C. at 0.08 mm.;
N-Nethyl-N-[4-(dimethylamino)-2-butynyl]propionamide, which distilled at 92.0° C. at 0.05 mm.;
N-(4-Pyrrolidino-2-butynyl)nicotinamide;
N-Methyl-N-[4-(1-pyrrolidinyl)-2-butynyl]propionamide, which distilled at 116.0° C. at 0.05 mm.;
N-(3-Methoxypropyl)-N-[4(1-pyrrolidinyl)-2-butynyl]-formamide, which distilled at 140.0° C. at 0.05 mm.;
N-(3-Methoxypropyl)-N-[4-(butylmethylamino)-2-butynyl]-formamide, which distilled at 142.0° C. at 0.05 mm.;
N-(4-Diethylamino-2-butynyl)-2-pyrrolidinone, which distilled at 115° C. at 0.04 mm.;
N-(4-Diisopropylamino-2-butynyl)-2-pyrrolidinone, which distilled at 123° C. at 0.04 mm.;
N-[4-(Methylpropylamino)-2-butynyl]-2-pyrrolidinone, which distilled at 123° C. at 0.07 mm.;
N-(4-Dimethylamino-2-butynyl)-2-pyrrolidinone, which distilled at 104° C. at 0.03 mm.;
N-(4-Diallylamino-2-butynyl)-2-pyrrolidinone, which distilled at 122° C. at 0.05 mm.;
N-[4-(Benzylmethylamino)-2-butynyl]-2-pyrrolidinone, which distilled at 148° C. at 0.04 mm.;
N-(4-Diisobutylamino-2-butynyl)-2-pyrrolidinone, which distilled at 129° C. at 0.03 mm.;
N-[4-(Isopropylmethylamino)-2-butynyl]-2-pyrrolidinone, which distilled at 126° C. at 0.04 mm.;
N-[4-(Isopentylmethylamino)-2-butynyl]-2-pyrrolidinone, which distilled at 127° C. at 0.03 mm.;
N-(Dipropylamino-2-butynyl)-2-pyrrolidinone, which distilled at 110° C. at 0.03 mm.;
N-[4-(Butylmetylamino)-2-butynyl]-2-pyrrolidinone, which distilled at 110° C. at 0.03 mm.;
N-(4-Dioctylamino-2-butynyl)-2-pyrrolidinone, which distilled at 162° C. at 0.04 mm.;
N-(4-Dicyclohexyl-2-butynyl)-2-pyrrolidinone, which distilled at 162° C. at 0.05 mm.;
N-[4-(Benzylisopropylamino)-2-butynyl]-2-pyrrolidinone, which distilled at 154° C. at 0.04 mm.;
N-[4-(Butylethylamino)-2-butynyl]-2-pyrrolidinone, which distilled at 132.0° C. at 0.06 mm.;
N-[4-(N,α-Dimethylphenethylamino)-2-butynyl]-2-pyrrolidinone, which distilled at 160° C. at 0.06 mm.;
N-[4-(bis[2-Hydroxypropyl]amino)-2-butynyl]-2-pyrrolidinone, which distilled at 192.0° C. at 0.06 mm.;
N-[4-(Ethylpropylamino)-2-butynyl]-2-pyrrolidinone, which distilled at 122.0° C. at 0.06 mm.;
N-[4-(bis[2-Methyl-2-propenyl]amino)-2-butynyl]-2-pyrrolidinone, which distilled at 126° C. at 0.05 mm.;
N-[4-Butylmethylamino)-2-butynyl]-3-thiamorpholinone, which distilled at 145.0° C. at 0.05 mm.;
N-[4-(Methyl[tetrahydrofuryl])-2-butynyl]-2-pyrrolidinone, which distilled at 142° C. at 0.05 mm.;
N-[4-(Butylmethylamino)-2-butynyl]-5-methyl-2-pyrrolidinone, which distilled at 128.0° C. at 0.05 mm.;
N-[4-(Methyl[α-methylphenethyl]amino)-2-butynyl]-2-oxazolidinone, which distilled at 184.0° C. at 0.66 mm.;

N-[4-(3-Pyrrolin-1-yl)-2-butynyl]succinimide, a solid which melted at 136.8–140.6° C.;
N-[4-(Diisopropylamino)-2-butynyl]succinimide, as white crystals which melted at 54.2°–55.6° C.;
N-[4-(2,5-Dimethyl-1-pyrrolidinyl)-2-butynyl]succinimide, as white needles which melted at 65.0°–67.0° C.;
N-(4-Hexamethyleneimino-2-butynyl)-2-pyrrolidinone, which distilled at 156° C. at 0.3 mm.;
N-(4-Piperidino-2-butynyl)-2-pyrrolidinone, which distilled at 141° C. at 0.12 mm.; the picrolonate acid-addition salt of this compound was obtained as a yellow solid which melted at 147.0°–148.85° C.;
N-(4-Morpholino-2-butynyl)-2-pyrrolidinone, which distilled at 161° C. at 0.04 mm.;
N-[4-(4-methyl-1-piperazinyl)-2-butynyl]-2-pyrrolidinone, which distilled at 143° C. at 0.06 mm.;
N-(4-Heptamethyleneimino-2-butynyl)-2-pyrrolidinone, which distilled at 153° C. at 0.03 mm.;
N-[4-(1,2,3,6-Tetrahydro-4-phenyl-1-pyridyl)-2-butynyl]-2-pyrrolidinone, a white solid which melted at 65.8°–67.4° C.;
N-[4-(3-Pyrrolin-1-yl)-2-butynyl]-2-pyrrolidinone, which distilled at 130° C. at 0.03 mm.;
N-[4-(2,5-Dimethyl-1-pyrrolidinyl)-2-butynyl]-2-pyrrolidinone, which distilled at 125° C. at 0.03 mm.;
N-(4-Octamethyleneimino-2-butynyl)-2-pyrrolidinone, which distilled at 166.0° C. at 0.06 mm.;
N-(4-Pyrrolidino-2-butynyl)-hexahydro-2H-azepin-2-one, which distilled at 134° C. at 0.03 mm.;
N-(4-Pyrrolidino-2-butynyl)-3-thiamorpholinone, which distilled at 155.0° C. at 0.05 mm.;
N-(4-Pyrrolidino-2-butynyl)-2-oxazolidinone, which distilled at 146° C. at 0.07 mm.;
N-(4-Piperidino-2-butynyl)-hexahydro-2H-azepin-2-one, which distilled at 157° C. at 0.03 mm.;
N-(4-Pyrrolidino-2-butynyl)propionamide, which distilled at 132.0° C. at 0.05 mm.;
N-[4-(Dimethylamino)-2-butynyl]propionamide, which distilled at 114.0° C. at 0.05 mm.;
N-(4-Pyrrolidino-2-butynyl)-3,4,5-trimethoxy-benzamide, m.p. 101.6°–103.0° C.;
5-Methyl-1-(4-pyrrolidino-2-butynyl)-2-pyrrolidinone, which distilled at 125.0° C. at 0.06 mm.;
N-(4-Pyrrolidino-2-butynyl)-2-piperidinone, which distilled at 131° C. at 0.03 mm.;
N-(4-Pyrrolidino-2-butynyl)phthalimide m.p. 113.0°–115.0° C;
5-Chloro-N-(4-piperidino-2-butynyl)phthalimide;
5-Methylmercapto-N-(4-morpholino-2-butynyl)phthalimide;
4,5,6,7-Tetrachloro-N-(4-dimethylamino-2-butynyl)-phthalimide;
5-Methoxy-N-(4-pyrrolidino-2-butynyl)phthalimide;
4-Bromo-N-(4-pyrrolidino-2-butynyl)phthalimide;
1-[4-(Benzylmethylamino)-2-butynyl]pyrrolidine, which distilled at 122.0° C. at 0.05 mm.;
o-Xylylenebis[1-(2-pyrrolidinone)], which melted at 122.8°–125.0° C.;
N-[4-(Dicyclohexylamino)-2-butynyl]propionamide;
N-[4-(N-Cyclohexyl-N-methylamino)-2-butynyl]propionamide;
N-[4-(N-Allyl-N-ethylamino)-2-butynyl]acetamide;
N-[4-(Diallylamino)-2-butynyl]acetamide;
N-[4-(N-Benzyl-N-methylamino)-2-butynyl]acetamide;
N-[4-(N-[4-Tolylmethyl]-N-ethylamino)-2-butynyl]propionamide;

N-[4-(N-[2-Chlorobenzyl]-N-propylamino)-2-butynyl]-butyramide;
N-(4-Dicyclohexylamino-2-butynyl)phthalimide;
N-(4-Diallylamino-2-butynyl)phthalimide
N-[4-(N-Benzyl-N-methylamino)-2-butynyl]phthalimide,
N-[4-(N-Cyclopentyl-N-methylamino)-2-butynyl]phthalimide; and
N-[4-(N-Allyl-N-methylamino)-2-butynyl]phthalimide.

I claim:

1. A compound of the formula

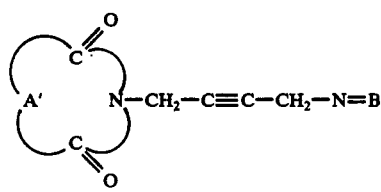

wherein A' is a member of the group consisting of divalent alkylene of from two to four carbon atoms and unsubstituted orthophenylene, and N=B is a basic tertiary amino radical selected from the group consisting of di(lower-alkyl)amino, N-lower-alkyl-N-lower-alkenylamino, di(lower-alkenyl)amino, N-lower-alkyl-N-cycloalkylamino, di(cycloalkyl)amino, N-(phenyl-lower-alkyl)-N-lower-alkylamino, pyrrolidino, piperidino, morpholino, and thiamorpholino.

2. N-(4-Pyrrolidino-2-butynyl)phthalimide, according to claim 1 wherein A' is unsubstituted ortho-phenylene and N=B is pyrrolidino.

3. N-(4-Pyrrolidino-2-butynyl)succinimide, according to claim 1 wherein A' is ethylene and N=B is pyrrolidino.

4. N-(5-Diisopropylamino-3-butynyl)succinimide, according to claim 1 wherein A' is ethylene and N=B is diisopropylamino.

5. A compound selected from the group consisting of

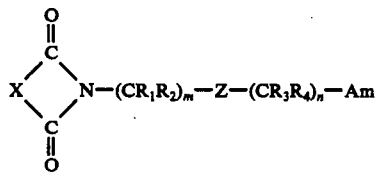

and non-toxic addition salts thereof, wherein X is $(CHR_5)_p$, p being an integer from 2 to 3, each $R_5$ being selected from the class consisting of hydrogen and alkyl, $R_1$, $R_2$, $R_3$ and $R_4$ are each hydrogen, m and n are the integer 1, Z is the divalent radical —C≡C—, and Am is an amino group joined to the linking chain at the N atom, the amino group being selected from the class consisting of di-alkyl amino, di-alkenyl amino, (alkyl, alkenyl)amino, pyrrolidino, piperidino, methyl substituted pyrrolidino having 1 to 2 methyl groups, and morpholino, said alkyl and alkenyl groups when present having from 1 to 5 carbon atoms.

6. A compound according to claim 5 wherein X is selected from the group consisting of

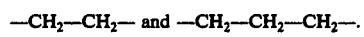

—CH₂—CH₂— and —CH₂—CH₂—CH₂—.

7. A compound according to claim 6 selected from the class consisting of N-(4-pyrrolidino-2-butynyl)-succinimide and pharmaceutically acceptable additional salts thereof.

8. A process for the preparation of the formula

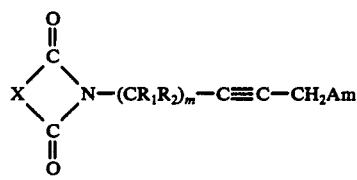

and non-toxic addition salts thereof wherein X is $(CHR_5)_p$, p being an integer from 2 to 3, each $R_5$ being selected from the group consisting of hydrogen and alkyl, $R_1$ and $R_2$ are each hydrogen, m is the integer 1 and Am is an amino group joined to the linking chain at the nitrogen atom, the amino group being selected from the class consisting of di-alkyl amino, d-alkenyl amino, (alkyl, alkenyl) amino, pyrrolidino, piperidino, methyl substituted pyrrolidino having 1 to 2 methyl groups, and morpholino, and alkyl and alkenyl groups when present having from 1 to 5 carbon atoms, the system of reaction of propargyl imide of the formula

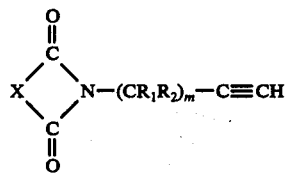

with formaldehyde and an amine of the formula HAm, $R_1$, $R_2$ and Am being as defined above.

* * * * *

UNITED STATES PATENT OFFICE
CERTIFICATE OF CORRECTION

Patent No. 4,065,471  Dated December 27, 1977

Inventor(s) William B. Dickinson

It is certified that error appears in the above-identified patent and that said Letters Patent are hereby corrected as shown below:

Column 3, line 40 below the formula insert --Formula IV--.

Column 11, line 35 reads "N-(5-Diisopropylamino-3-butynyl)succinimide," and should read --N-(4-Diisopropylamino-2-butynyl)succinimide,--.

*Signed and Sealed this*

*Twenty-sixth* Day of *September 1978*

[SEAL]

Attest:

RUTH C. MASON
*Attesting Officer*

DONALD W. BANNER
*Commissioner of Patents and Trademarks*